United States Patent [19]

Brayer et al.

[11] Patent Number: 5,744,635
[45] Date of Patent: Apr. 28, 1998

[54] PREPARATION PROCESS FOR BETA-ALKOXY ACRYLIC ACID

[75] Inventors: Jean-Louis Brayer, Nanteuil-Le-Haudouin, France; David Michael Hodgson, Reading, Great Britain; Ian Christopher Richards, Saffron Walden, Great Britain; Jason Witherington, Reading, Great Britain

[73] Assignee: Roussel Uclaf, France

[21] Appl. No.: 532,784

[22] PCT Filed: Apr. 14, 1994

[86] PCT No.: PCT/FR94/00418

§ 371 Date: Oct. 3, 1995

§ 102(e) Date: Oct. 3, 1995

[87] PCT Pub. No.: WO94/24085

PCT Pub. Date: Oct. 27, 1994

[30] Foreign Application Priority Data

Apr. 15, 1993 [FR] France ................................. 93 04439
Jan. 27, 1994 [GB] United Kingdom ................. 9401541

[51] Int. Cl.[6] ................................................ C07C 69/73
[52] U.S. Cl. ....................... 560/183; 560/60; 560/9; 546/34.1
[58] Field of Search ................... 560/60, 183, 9; 546/341

[56] References Cited

FOREIGN PATENT DOCUMENTS 60-116650  6/1985  Japan .

OTHER PUBLICATIONS

Chemical Abstracts Service Registry Handbook. Number Section. 1985 Supplement. ACS, Columbus, Ohio. RN=99503-30-7, RN=99503-34-1, 1985.

Synthetic Communications, 11(7), pp. 513–518, (1981) The Palladium–Catalyzed Cross–Coupled Reaction . . . of Bases, N. Miyaura, et al, Japan J.C.S. Chem. Comm., (1979).

Stereoselective Synthesis of Arylated . . . Palladium Catalyst, N. Miyaura, et al, pp. 866–867, (Japan).

Primary Examiner—Gary Geist
Assistant Examiner—Sreeni Padmanabhan
Attorney, Agent, or Firm—Bierman, Muserlian and Lucas

[57] ABSTRACT

A method for prerparing compounds of formula (I), wherein R is an optionally substituted alkenyl or alkynyl radical having up to 8 carbon atoms, or an optionally substituted mono- or polycyclic aryl or heteroaryl radical, and $R_1$ and $R_2$ are an alkyl radical having up to 4 carbon atoms. According to the method, a compound of the formula (II), wherein X is a halogen atom, is exposed to an organometallic compound of the formula (III): RZ, wherein R has the same meaning as before and Z is a metal or metal derivative. Alternatively, a compound of formula (II'), wherein Z' is a metal or metal derivative, is exposed to a compound of the formula (III'): RX', wherein X' is a nucleophilic reaction leaving group.

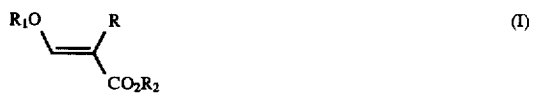

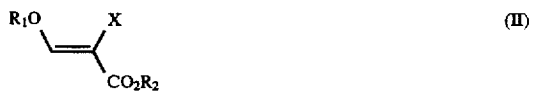

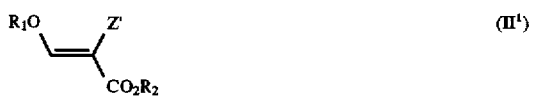

24 Claims, No Drawings

PREPARATION PROCESS FOR BETA-ALKOXY ACRYLIC ACID

This is the U.S. National Stage Application of PCT/FR94/00418 filed Apr. 14, 1994 now WO94/24085 published Oct. 27, 1994.

The present invention relates to a preparation process for derivatives of beta-alkoxy acrylic acid.

A subject of the invention is a preparation process for compounds of formula (I):

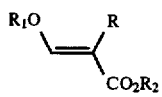
(I)

in which R represents an optionally substituted alkenyl or alkynyl radical containing up to 8 carbon atoms, an optionally substituted monocyclic or polycyclic aryl or heteroaryl radical, $R_1$ and $R_2$, identical or different, represent an alkyl radical containing up to 4 carbon atoms, characterized in that a compound of formula (II):

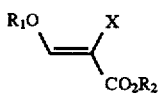
(II)

in which X represents a halogen atom, is subjected to the action of an organometallic compound of formula (III):

RZ                                          (III)

in which R retains its previous meaning and Z represents a metal or a metallic derivative, or a compound of formula (II'):

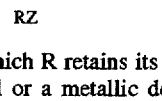
(II')

in which Z' represents a metal or a metallic derivative and $R_1$ and $R_2$ have the definition indicated previously, is subjected to the action of a compound of formula (III'):

RX'                                    (III')

in which R retains its previous meaning and X' represents a nucleophilic reaction leaving group, in order to obtain the corresponding compound of formula (I).

By alkyl radical represented by $R_1$ and $R_2$ is meant a methyl, ethyl, linear or branched propyl, linear or branched butyl radical.

When R represents an alkenyl radical, it is preferably a vinyl, allyl, butenyl, pentenyl, hexenyl, or cyclohexenyl radical.

When R represents an alkynyl radical, it is preferably an ethynyl, propargyl or butynyl radical.

When R represents an aryl radical, it is preferably the phenyl or naphthyl radical.

When the alkenyl or alkynyl radical is substituted, it is for example an alkoxylated substituent such as methoxy, ethoxy, propyloxy.

When R represents a heterocyclic aryl radical, it is preferably a heterocyclic radical with 5 members such as one of the following radicals: thienyl, furyl, pyrrolyl, thiazolyl, oxazolyl, imidazolyl, thiadiazolyl, thiazolidinyl, dioxolannyl, pyrazolyl, oxazolyl or isoxazolyl, or also a heterocyclic radical with 6 members, such as the pyridyl, pyrimidinyl, pyridazinyl or pyrazinyl radical, or also a condensed aryl radical such as the indolyl, benzofuryl, benzothienyl, benzothiazolyl, quinolinyl, quinazolinyl or dihydroquinazolinyl radical.

When R is a a substituted aryl or heteroaryl radical, it is preferably substituted by one or more radicals chosen from the group constituted by free, salified, esterified or amidified carboxy radicals, hydroxyl radicals, halogen atoms, $NH_2$, $NO_2$, C≡N, alkyl, alkenyl, alkynyl, aryl and heteroaryl radicals, O-alkyl, O-alkenyl, O-alkynyl, O-aryl and O-heteroaryl radicals, S-alkyl, S-alkenyl, S-alkynyl, S-aryl and S-heteroaryl radicals and N-alkyl, N-alkenyl, N-alkynyl, N-aryl and N-heteroaryl radicals containing up to 24 carbon atoms, optionally substituted by one or more halogen atoms, the radical

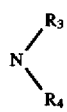

and the radical $-S(O)_t-R_5$, $R_3$ and $R_4$, identical or different, and $R_5$ representing a hydrogen atom or an alkyl or aryl radical containing up to 12 carbon atoms, optionally substituted, and t representing the number 0, 1 or 2.

By halogen atom is meant for example a fluorine, chlorine, bromine or iodine atom.

By alkyl, alkenyl, alkynyl, aryl or heteroaryl radical which can be represented by the substituents of the aryl or heteroaryl radical or be contained in these substituents, is preferably meant one of those indicated above for $R_1$, $R_2$ or R.

By esterified carboxy radical is meant for example methoxycarbonyl or ethoxycarbonyl.

By salified carboxy radical is meant for example a radical salified by a sodium or potassium atom.

X represents a fluorine, chlorine, bromine or iodine atom.

When Z represents a metal, it is an alkali metal such as lithium, sodium or potassium.

When Z represents a metallic derivative, it is a derivative of an alkaline-earth metal or of a metal with a higher valency such as magnesium, calcium, titanium, nickel, copper, zinc, aluminium, boron, tin, palladium or platinum.

By derivative is meant a hydroxylated, alkoxylated, alkylated derivative or a halide, or also a halogen-containing alkylated or halogen-containing hydroxylated derivative.

By metal or metallic derivative which is represented by Z' is meant one of those indicated above for Z.

By nucleophilic reaction leaving group which is represented by X' is meant for example a halogen atom, preferably a bromine or iodine atom, or an $-O-SO_2-Q$ group in which Q represents a $CF_3$, $(CF_2)_m-CF_3$ group in which m represents a number comprised between 2 and 9, a terbutyl or aryl group in which aryl is defined as above.

A particular subject of the invention is a process characterized in that in the compound of formula (II) used as the starting product, x represents a bromine or iodine atom.

A particular subject of the invention is a process in which Z represents an alkali metal or an alkaline-earth metal derivative, tin, boron or zinc.

A more particular subject of the invention is a process characterized in that in the compound of formula RZ used as the starting product, Z is chosen from the group constituted by Li, Na, K, $MgHal_1$, $ZnHal_2$, $Sn(R')_3$, $B(OH)_2$, $B(OR'')_2$, $B[O(CH_2)_nO]_2$, $Hal_1$ and $Hal_2$ representing a halogen atom, R' and R'' representing a linear or branched alkyl radical containing up to 4 carbon atoms and n representing an integer equal to 1, 2, 3 or 4, and quite particularly a process in which Z is a derivative of boron such as $B(OH)_2$, or also a process in which Z is a derivative of tin such as Sn(R')₃, R' being defined as previously, for example Sn(Bu)₃.

Also a particular subject of the invention is a process characterized in that in the compound of formula (II'), Z' represents a derivative of tin, zinc, copper, palladium or platinum and preferably, a derivative of tin Sn(R')₃ defined as previously, for example Sn(Bu)₃.

Also a particular subject of the invention is a process characterized in that the compound of formula (III') is a halogenated derivative and more particularly an iodinated derivative.

A quite particular subject of the invention is a process characterized in that the reaction between the compounds of formulae (II) and (III) and formulae (II') and (III') takes place in the presence of a palladium catalyst, or a platinum catalyst or if desired in the presence of other catalysts.

Among the preferred processes of the invention, there can be mentioned the process characterized in that the palladium catalyst is chosen from the group constituted by Pd(OAc)₂, PdCl₂, Pd(Pϕ₃)₄, PdCl₂(CH₃CN)₂, or also tris (dibenzylidene) dipalladium. There can be mentioned in particular the process characterized in that the catalyst is Pd(Pϕ₃)₄; there can also be mentioned the process characterized in that the reaction between the compounds of formulae (II) and (III) and formulae (II') and (III') takes place in the presence of a ligand. The ligand is preferably a phosphine such as trifurylphosphine, an arsine such as triphenylarsine or also acetonitrile or benzonitrile. A quite particular subject of the invention is the process characterized in that the ligand is a phosphine chosen from the group constituted by P(Ar)₃ and Pd(Pϕ₃)₄.

The palladium and the ligand can be part of the same chemical entity in the case where Pd (Pϕ₃)₄ is used for example.

Among the processes of the invention there can also be mentioned a process characterized in that the reaction between the compounds of formula (II) and of formula (III) takes place in the presence of a base, for example a base chosen from the group constituted by Na₂CO₃, Ba(OH)₂, NaOH, CaCO₃, CsCO₃ and K₃PO₄ and quite particularly Na₂CO₃.

Among the processes of the invention, there can also be mentioned a process characterized in that the reaction between the compounds of formula (II') and of formula (III') takes place in the presence of a copper salt, in particular cuprous iodide.

When a compound of formula (II) in which X represents a bromine or iodine atom, is subjected to the action of a compound of formula (III) in which Z represents a boron derivative, the coupling kinetics can be considerably increased by adding a phase transfer agent, for example triethylbenzylammonium chloride.

The compounds of formula (II) used as starting products of the process of the invention are new products and are in themselves a subject of the present invention: they can be prepared according to the following reaction diagram:

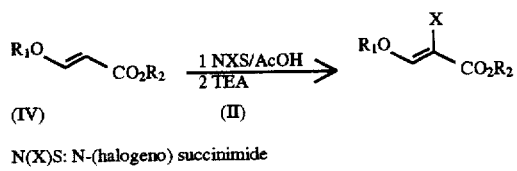

N(X)S: N-(halogeno) succinimide in which X, R₁ and R₂ have the meaning indicated previously.

A quite particular subject of the invention is methyl 2-iodo 3-methoxy 2-propenoate and methyl 2-bromo 3-methoxy 2-propenoate.

The products of formula (IV) are known products described for example in Tetrahedron letters Vol. 34 No. 47 p. 5209–5210 (1983).

The compounds of formula (III) are obtained in a standard manner from corresponding halogenated derivatives according to the process described for example in Advanced Organic Chemistry 2nd Edition p. 566–569.

The compounds of formula (II') used as starting products of the process of the invention described above are new products and are in themselves a subject of the present invention: they can be prepared by organometallic coupling starting from the halogenated compound of formula (II) in an organic solvent in the presence of a palladium catalyst. An example of such a preparation is given hereafter in the experimental part.

The compounds of formula (III') are known products, described in the literature or commercial products.

The process of the invention is of great industrial interest, it allows the compounds of formula (I), and in particular the derivatives substituted in ortho position, to be prepared in a stereospecific manner in a single stage.

The compounds of formula (I) are products known in a general manner described for example in the European Patent 178826.

The following examples illustrate the invention without however limiting it.

EXAMPLE 1

Methyl (E) alpha-(methoxymethylene) 4-methylbenzene acetate 1.44 g of methyl 2-iodo 3-methoxy 2-propenoate obtained as indicated in Preparation 1, 1.22 g of 4-methyl phenylboronic acid, 30 ml of toluene, 0.34 g of tetra t-riphenylphosphine palladium Pd(Pϕ₃)₄ and 6 ml of a 2M sodium carbonate solution are taken to reflux for 3 hours. The reaction medium is filtered and rinsed with ethyl acetate. Extraction is carried out with ethyl acetate, the extracts are washed with an ammonium chloride solution, the organic phases are dried, filtration is carried out and the solvent is eliminated under reduced pressure. 2.06 g of product is obtained which is treated with activated charcoal and recrystallization is carried out from a solution of isopropyl ether and pentane (20–80). In this way 1.06 g of product is obtained melting at 65° C.

EXAMPLE 2

Methyl (E) alpha-(methoxymethylene) 3-chloro 4-fluoro benzene acetate

A mixture of 1.44 g of methyl 2-iodo 3-methoxy 2-propenoate, 1.57 g of 3-chloro 4-fluorophenyl boronic acid, 30 ml of toluene, 0.07 g of palladium acetate, 0.16 g of triphenylphosphine, 2 ml of methanol and 10 ml of a 2M sodium carbonate solution is taken to reflux for one hour 30 minutes. The mixture is filtered and rinsed with ethyl acetate. Extraction is carried out with ethyl acetate and the extracts are washed with an ammonium chloride solution. The organic phases are dried and filtration is carried out. After concentrating under reduced pressure, 2.17 g of a product is obtained which is chromatographed on silica (eluant: heptane-ethyl acetate 85–15). 1.25 g of product is obtained which is treated with activated charcoal and recrystallization is carried out from isopropyl alcohol. In this way 1.16 g of desired product is obtained. M.p.=85.9° C.

EXAMPLE 3

Methyl (E) alpha-(methoxymethylene) 2-methylbenzene acetate

STAGE A: 2-(2-methylphenyl) 1,3,2-dioxaborinane

A mixture of 1.75 g of 2-methyl phenylboronic acid trimer, 30 ml of cyclohexane, and 0.5 ml of 1,3-propanediol is heated under reflux for 6 hours. The mixture is washed with water and extracted with pentane. The organic phases are dried and concentrated under reduced pressure. In this way 1.8 g of desired product is obtained.

STAGE B: methyl (E) alpha-(methoxymethylene) 2-methylbenzene acetate

A mixture of 0.73 g of methyl 2-iodo 3-methoxy 2-propanoate, 1.02 g of the product prepared in Stage A, 20 ml of dimethylformamide, 0.12 g of tetra triphenylphosphine palladium Pd(Pφ$_3$)$_4$ and 1.6 g of tripotassium phosphate is taken to 80° C. for one hour. The reaction mixture is poured onto ice and extracted with isopropyl ether. After extraction, washing and drying, the organic phases are filtered, followed by concentrating under reduced pressure. 1.16 g of product is obtained which is treated with activated charcoal and recrystallization is carried out from pentane. In this way 0.54 g of desired product is obtained, melting at 43.5° C.

EXAMPLE 4

Methyl (E) alpha-(methoxymethylene) 2,4-dichlorobenzene acetate.

A mixture of 1.44 g of methyl 2-iodo 3-methoxy 2-propenoate, 1.73 g of 2,4-dichlorophenyl boronic acid, 30 ml of toluene, 0.11 g of triethyl benzyl ammonium chloride (TEBAC), 0.30 g of tetrakis triphenyl phosphine palladium and 10 ml of a 2M sodium carbonate solution is taken to reflux for 4 hours. After filtration, extraction is carried out with ethyl acetate and the extracts are washed with an ammonium chloride solution. The organic phases are dried and filtration is carried out. After concentrating under reduced pressure, 2.17 g of a product is obtained which is chromatographed on silica (eluant: heptane-ethyl acetate 85-15). The crude product is obtained which is recrystallized from a solution of isopropyl alcohol and pentane 20-80. 1.31 g of desired product is obtained. M.p.=82.1° C.

EXAMPLE 5

Methyl (E) alpha-(methoxymethylene) 2-methylbenzene acetate.

A mixture of 5 ml of methyl 2-(tributyltin) 3-methoxy 2-propenoate obtained as in Preparation 3, 1.09 g of 2iodotoluene, 0.57 g of tetrakis (triphenylphosphine) palladium, 0.71 g of cuprous iodide in 50 ml of dimethylformamide is taken to 80° C. for 24 hours. After filtration, the solvent is evaporated off under reduced pressure, the residue is taken up in 100 ml of ethyl acetate, a saturated solution of potassium fluoride is added, followed by filtration, the organic phase is washed with a saturated aqueous solution of sodium chloride, dried and the solvent is evaporated off under reduced pressure. After chromatography on silica (eluant: hexane-ethyl acetate 75-25), 0.57 g of crude product is collected which is recrystallized from pentane. 0.5 g of expected product is obtained. M.p.=43° C.

According to the diagram

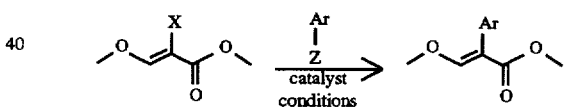

by operating as in Example 1, the following were obtained:

| Ex. | Ar | Z | X | Catalyst | Conditions | Yield % | M.P. °C. |
|---|---|---|---|---|---|---|---|
| 6 | phenyl | B(OH)2 | I | Pd(Pφ$_3$)$_4$ | Na$_2$CO$_3$(2M) | 95 | 124.5 |
| 7 | 4-chlorophenyl | " | " | " | " | 93 | 63.7 |
| 8 | 3-nitrophenyl | " | " | " | " | 53 | 104.4 |
| 9 | 2,4-dichloro-phenyl | " | " | " | " | 52 | 82.1 |
| 10 | 2,4-dimethyl-phenyl | " | " | " | " | 83 | 67 |
| 11 | naphthyl | " | Br | " | " | 79 | 125 |
| 12 | naphthyl | " | I | " | " | 89 | 125 |
| 13 | vinyl | Sn(Bu)$_3$ | " | " | — | 76 | — |
| 14 | 1-methoxyvinyl | " | " | " | — | 82 | — |
| 15 | 2-pyridyl | " | " | " | — | 10 | — |

By operating as in Example 3, the following were obtained:

| Ex. | Ar | Z | X | Catalyst | Conditions | Yield % | M.P. °C |
|---|---|---|---|---|---|---|---|
| 16 | 2-[2,4-dichloro-phenoxy] phenyl | B(OH)$_2$ | I | Pd(PΦ$_3$)$_4$ | K$_3$PO$_4$ | 72 | — |
| 17 | 2-phenoxyphenyl | " | " | " | " | 88 | — |

By operating as in Example 2, the following were obtained:

| Ex. | Ar | Z | X | Catalyst | Conditions | Yield % | M.P. °C |
|---|---|---|---|---|---|---|---|
| 18 | 3,5-dichloro-phenyl | B(OH)$_2$ | I | Pd(OAc)2 2PΦ$_3$ | Na$_2$CO$_3$(2M) | 79 | 126.5 |
| 19 | 4-fluorophenyl | " | " | " | " | 86 | 86.2 |
| 20 | 3,5-bis(trifluoro-methyl) phenyl | " | " | " | " | 72 | — |
| 21 | 2-methylphenyl | " | " | " | " | 58 | 43.5 |
| 22 | 4-bromophenyl | " | " | " | " | 65 | 58.3 |
| 23 | 4-methoxyphenyl | " | " | " | " | 78 | 63 |
| 24 | naphthyl | " | " | " | " | 72 | 125 |
| 25 | 2-phenoxyphenyl | " | " | " | " | 52 | — |

By operating as in Example 4, the following were obtained:

| Ex. | Ar | Z | X | Catalyst | Conditions | Yield % | M.P. °C |
|---|---|---|---|---|---|---|---|
| 26 | 2-methylphenyl | B(OH)$_2$ | I | Pd(PΦ$_3$)$_4$ | Na$_2$CO$_3$(2M) + TEBAC | 95 | 43.4 |
| 27 | 2-isopropyl-phenyl | " | " | " | " | 79 | — |
| 28 | 2-methyl 3-fluorophenyl | " | " | " | " | 73 | 65.9 |
| 29 | 2-methyl 4-fluorophenyl | " | " | " | " | 80 | 65.5 |
| 30 | 2-methyl 5-fluorophenyl | " | " | " | " | 75 | 53.2 |

According to the diagram

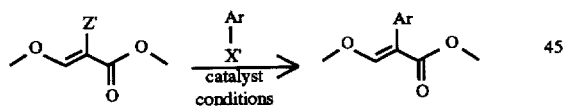

by operating as in Example 5, the following were obtained:

| Ex. | Ar | Z' | X' | Catalyst | Conditions | Yield % | M.P. °C |
|---|---|---|---|---|---|---|---|
| 31 | 7-(2,2-dimethyl 3-butynyl) naphthyl | Sn(BU)$_3$ | I | Pd(PΦ$_3$)$_4$ | CuI | 75 | 171.5 |

EXAMPLE 32

Methyl 3-methoxy 2-(4-methylphenyl) acrylate.

63 mg of 4-iodotoluene is added under agitation to a solution containing 292 mg of the product obtained in Preparation 4 and 100 mg of tetrakis (triphenylphosphine) palladium in 7 cm$^3$ of dimethylformamide. After 5 minutes, 42 mg of copper iodide is added and the mixture is agitated for 16 hours protected from the light. An aqueous solution of sodium chloride then a 1-1 mixture of petroleum ether (B.p. 40°/60° C.) and ethyl ether are added. The organic phases are combined, dried and evaporated under reduced pressure. The residue is chromatographed on silica (eluant: ethyl acetate-petroleum ether 4-1) and 43 mg of expected product is obtained.

EXAMPLE 33

Methyl 3-methoxy 2-(2-methylthiophenyl) acrylate.

41 mg of 1-iodo 2-methylthiobenzene is added under agitation to a solution containing 100 mg of the product obtained in Preparation 4, 23 mg of copper iodide, 25 mg of tris(dibenzylidene) dipalladium and 11 mg of triphenyl arsine in 5 ml of N-methylpyrrolidinone. The reaction medium is heated at 50° C. for 48 hours under an inert atmosphere and protected from the light. The reaction medium is treated as indicated in Example 1 and the expected product is obtained with a yield of 79%.

EXAMPLE 34

Methyl (E) 3-methoxy 2-(2-phenoxyphenyl) acrylate.

By operating as in Example 33 starting with 1-iodo 2-phenoxybenzene, the expected product was obtained in the form of an oil.

EXAMPLE 35

Methyl (E) 3-methoxy 2-[(2-phenoxymethyl) phenyl] acrylate.

By operating as in Example 33 starting with 1-iodo 2-(phenoxymethyl) benzene, the expected product was obtained. M.p.=55° C.

EXAMPLE 36

Methyl (E) 3-methoxy 2-[2-(phenylmethylthio) phenyl] acrylate.

By operating as in Example 33 starting with 1-iodo 2-(phenylmethylthio) benzene, the expected product was obtained. M.p.=72°–74° C.

EXAMPLE 37

Methyl (E) 3-methoxy 2-[3-methyl 2-(phenylmethylthio) phenyl] acrylate.

By operating as in Example 33 starting with 1-iodo 3-methyl 2-(phenylmethylthio) benzene, the expected product was obtained. M.p.=119°–120° C.

EXAMPLE 38

Methyl 3-methoxy 2-(2-thiophenyl) acrylate.

By operating as in Example 33 starting with 2-iodo thiophene, the expected product was obtained in the form of an oil containing a 2/1 mixture of E and Z isomers which is purified by chromatography on silica.

Preparation 1: methyl 2-iodo 3-methoxy 2-propenoate

A solution containing 12.95 g of methyl 3-methoxy 2-propenoate and 50 ml of acetic acid is introduced into a solution containing 37 g of N-iodosuccinimide and 150 ml of acetic acid. The reaction medium is agitated for 4 hours at ambient temperature. It is concentrated under reduced pressure and taken up in isopropyl ether. Filtration and rinsing with isopropyl ether are carried out. After concentrating and taking up in methylene chloride, a sufficient quantity of triethylamine is added to ensure the conversion to the acrylic derivative. After washing, drying and concentrating, an oil is obtained which crystallizes spontaneously at ambient temperature. The crystals obtained are recrystallized from isopropanol. 17 g of desired product is obtained melting at 50.9° C.

Preparation 2: methyl 2-bromo 3-methoxy 2-propenoate

A mixture of 17 g of methyl 3-methoxy 2-propenoate, 200 ml of acetonitrile and 26.1 g of N-bromo succinimide is maintained under reflux for 2 hours.

2 g of N-bromosuccinimide is added and the reaction medium is taken to reflux again for 2 hours.

The reaction medium is concentrated under reduced pressure and taken up using an aqueous solution of sodium bicarbonate. Extraction is carried out with isopropyl ether, the extracts are washed, dried and concentrated. An oil is obtained which is distilled under reduced pressure. In this way 15 g of product is obtained which crystallizes spontaneously at ambient temperature.

The crystals obtained are recrystallized from pentane. In this way the desired product is obtained. M.p.=30.1° C. Microanalysis:

|    | Theoretical | Found |
|----|-------------|-------|
| C  | 30.79       | 30.8  |
| H  | 3.62        | 3.6   |
| Br | 40.98       | 40.8  |

Preparation 3: methyl 2-(tributyltin) 3-methoxy 2-propenoate.

10 g of methyl 2-iodo 3-methoxy 2-propenoate obtained as in Preparation 1 and 50 ml of hexabutylditin are heated under reflux for 12 hours in the presence of 1 g of bis (triphenyl phosphine) palladium chloride in 300 ml of dioxane. The solvent is eliminated under reduced pressure, the residue is taken up in 300 ml of ethyl acetate, a saturated solution of potassium fluoride is added, followed by filtration, the organic phase is washed with a saturated aqueous solution of sodium chloride, dried and the solvent is evaporated under reduced pressure. After chromatography on silica (eluant: hexane-ethyl acetate 98-2), 9.5 g of expected product is obtained.

Preparation 4: methyl E-3-methoxy 2-tri-n-butylstannyl propenoate.

100 mg of tetrakis (triphenylphosphine) palladium (O) is added under agitation at ambient temperature to a solution containing 750 mg of methyl 2-bromo 3-methoxy propenoate and 3.87 ml of bis (tri-n-butylene) in 5 ml of toluene. The mixture is heated under reflux and agitated for 24 hours. After cooling down, 30 ml of diethyl ether and 5 ml of a saturated aqueous solution of potassium fluoride are added and agitation is carried out for 15 minutes; filtration with celite is carried out, followed by washing with an aqueous solution of sodium chloride, drying over magnesium sulphate and evaporating under reduced pressure. The residue is purified by chromatography on silica (petroleum ether-ethyl acetate 95-5) and the expected product is obtained.

By operating in an identical manner to that described in Preparation 4, starting with methyl 2-iodo 3-methoxy propenoate, methyl E-3-methoxy 2-tri-n-butylstannyl propenoate was prepared.

We claim:

1. A process for the preparation of a compound of the formula

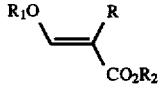   I wherein R is selected from the group consisting of optionally substituted alkenyl of 2 to 8 carbon atoms, optionally substituted alkynyl of 2 to 8 carbon atoms, optionally substituted phenyl and naphthyl and optionally substituted 5- and 6-membered heteroaryl having 1 or 2 heteroatoms and $R_1$ and $R_2$ are individually alkyl of 1 to 4 carbon atoms comprising reacting a compound of the formula

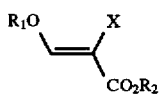   II wherein X is halogen with an organometallic compound of the formula

RZ   III wherein Z is a metal or metal derivative or reacting a compound of the formula

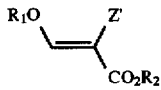

II wherein $R_1$ and $R_2$ are individually alkyl of 1 to 4 carbon atoms and Z' is a metal or metal derivative with a compound of the formula

RX'   III wherein R is defined as above and X' is a nucleophilic reaction leaving group to form a compound of Formula I.

2. Process according to claim 1, characterized in that X represents a bromine or iodine atom.

3. Process according to claim 1, characterized in that Z represents an alkali metal or a derivative of an alkaline-earth metal, of tin, of boron or of zinc.

4. Process according claim 1, characterized in that Z is chosen from the group constituted by Li, Na, K, $MgHal_1$, $ZnHal_2$, $Sn(R')_3$, $B(OH)_2$, $B(OR'')_2$, $B[O(CH_2)_nO]_2$, $Hal_1$ and $Hal_2$ representing a halogen atom, R' and R'' representing a linear or branched alkyl radical containing up to 4 carbon atoms and n representing an integer equal to 1, 2, 3 or 4.

5. Process according to claim 4, characterized in that Z is a boron derivative.

6. Process according to claim 5, characterized in that the boron derivative is $B(OH)_2$.

7. Process according to claim 4, characterized in that Z is a tin derivative $Sn(R')_3$, R' being defined as in claim 4.

8. Process according to claim 7, characterized in that the tin derivative is $Sn(Bu)_3$.

9. Process according to claim 1, characterized in that in the compound of formula (II'), Z' represents a derivative of tin, zinc, copper, palladium or platinum.

10. Process according to claim 9, characterized in that Z' is a tin derivative.

11. Process according to claim 9, characterized in that the tin derivative is $Sn(Bu)_3$.

12. Process according to claim 9, characterized in that the compound of formula (III') is a halogenated derivative.

13. Process according to claim 12, characterized in that the halogenated derivative is an iodinated derivative.

14. Process according to claim 1, characterized in that the reaction between the compounds of formulae (II) and (III) or of formulae (II') and (III') takes place in the presence of a palladium catalyst, or a platinum catalyst.

15. Process according to claim 1, characterized in that the palladium catalyst is chosen from the group constituted by $Pd(OAc)_2$, $PdCl_2$, $Pd(P\phi_3)_4$, $PdCl_2(CH_3CN)_2$ or tris (dibenzylidene) dipalladium.

16. Process according to claim 15, characterized in that the catalyst is $Pd(P\phi_3)_4$.

17. Process according to claim 1, characterized in that the reaction between the compounds of formulae (II) and (III) or of formulae (II') and (III') takes place in the presence of a ligand.

18. Process according to claim 17, characterized in that the ligand is a phosphine, an arsine, acetonitrile or benzonitrile.

19. Process according to claim 18, characterized in that the ligand is a phosphine chosen from the group constituted by $P(Q)_3$ and $Pd(P\phi_3)_4$.

20. Process according to claim 1, characterized in that the reaction between the compounds of formula (II) and of formula (III) takes place in the presence of a base.

21. Process according to claim 20, characterized in that the base is chosen from the group constituted by $Na_2CO_3$, $Ba(OH)_2$, NaOH, $CaCO_3$, $CsCO_3$ and $K_3PO_4$.

22. Process according to claim 21, characterized in that the base is $Na_2CO_3$.

23. Process according to claim 1, characterized in that the reaction between the compounds of formula (II') and of formula (III') takes place in the presence of a copper salt.

24. Process according to claim 23, characterized in that the copper salt is cuprous iodide.

* * * * *